США006440746B1

(12) United States Patent
Troxler et al.

(10) Patent No.: US 6,440,746 B1
(45) Date of Patent: *Aug. 27, 2002

(54) METHOD AND APPARATUS FOR ANALYZING ASPHALT CONTENT

(75) Inventors: Robert Ernest Troxler; William Finch Troxler, Sr., both of Raleigh; Wewage Linus Dep, Chapel Hill, all of NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/476,960

(22) Filed: Jan. 3, 2000

Related U.S. Application Data (63) Continuation-in-part of application No. 09/096,956, filed on Jun. 12, 1998, now Pat. No. 6,054,323.

(51) Int. Cl.[7] .............................................. G01N 31/12
(52) U.S. Cl. ..................... 436/155; 110/236; 110/345; 422/78; 436/60; 436/139; 436/145; 436/157; 436/160; 436/174; 436/181
(58) Field of Search ................................ 110/185, 190, 110/236, 345; 422/78, 99; 436/60, 145, 139–143, 155, 157, 160, 174, 181

(56) References Cited

U.S. PATENT DOCUMENTS

| | | |
|---|---|---|
| 2,010,460 A | 8/1935 | McKinley |
| 2,705,310 A | 3/1955 | Hodge |
| 2,798,928 A | 7/1957 | Friedberg |
| 2,855,494 A | 10/1958 | Kuehler |
| 4,028,527 A | 6/1977 | Thagard, Jr. |
| 4,043,048 A | 8/1977 | Veater |
| 4,164,655 A | 8/1979 | Noma et al. |
| 4,347,016 A | 8/1982 | Sindelar et al. |
| 4,874,950 A | 10/1989 | Regimand |

(List continued on next page.)

FOREIGN PATENT DOCUMENTS

| | | |
|---|---|---|
| DE | 38 08 888 A1 | 9/1989 |
| DE | 94 19 440 U1 | 5/1996 |
| EP | 0 501 847 A2 | 9/1992 |
| GB | 702578 | 1/1954 |
| WO | WO 94/23279 | 10/1994 |

OTHER PUBLICATIONS

Brown, et al., "Historical Development of Asphalt Content Determination by the Ignition Method", *Journal of the Association of Asphalt Paving Technolgist From the Proceedings of the Technical Sessions*, vol. 64 (Mar. 27–29, 1995), pp. 241–277.

Drüschner, L., *Bitumen*, 1993, vol. 55, pp. 158–162.

Todres and Bhattacharja, "Solvent–Free, Nuclear–Free Determination of Asphalt Content and Gradation of Hot–Mix Asphalt Concrete"; *The American Society for Testing and Materials* (Nov. 1994), vol. 22, pp. 564–570.

*Primary Examiner*—Arlen Soderquist
(74) *Attorney, Agent, or Firm*—Alston & Bird LLP (57) ABSTRACT

An apparatus for pyrolysis of a bituminous paving mix is provided, comprising an oven having a bottom wall, a top wall, and side walls defining a combustion chamber, a sample support within the combustion chamber, an infrared heater mounted within the oven and arranged for emitting infrared radiation towards the sample holder so as to heat a sample of paving mix by means of radiation heat transfer, an air inlet positioned for emitting air into the combustion chamber, and an outlet positioned to provide for the circulation of air and combustion gases through the combustion chamber. The apparatus may further include a blower located on the downstream side of the outlet for inducing flow into the combustion chamber by the inlet and out of the combustion chamber by the outlet. A variable speed blower controller may be used to vary the blower speed during paralysis of the paving mix. Both the temperatures of the infrared heater and the rate airflow through the chamber may be adjusted to minimize the time required to combust the asphalt binder.

49 Claims, 5 Drawing Sheets

U.S. PATENT DOCUMENTS

| | | |
|---|---|---|
| 5,081,046 A | 1/1992 | Schneider |
| 5,148,799 A | 9/1992 | St-Louis et al. |
| 5,151,601 A | 9/1992 | Regimand |
| 5,558,029 A | 9/1996 | Peake |
| 5,943,969 A | 8/1999 | Peake |
| 6,000,935 A | 12/1999 | Regimand et al. |
| 6,054,323 A * | 4/2000 | Troxler et al. ............... 436/155 |
| 6,190,917 B1 | 2/2001 | Barclay et al. |
| 6,207,462 B1 | 3/2001 | Barclay et al. |

* cited by examiner

METHOD AND APPARATUS FOR ANALYZING ASPHALT CONTENT

CROSS-REFERENCE TO RELATED APPLICATIONS

This is a continuation-in-part of U.S. patent application Ser. No. 09/096,956, filed on Jun. 12, 1998, now U.S. Pat. No. 6,054,323, which is herein incorporated by reference in its entirety.

FIELD OF THE INVENTION

The present invention relates to a method and apparatus for pyrolysis of a combustible material, and more particularly relates to a method and apparatus for pyrolysis of a bituminous paving mix.

BACKGROUND OF THE INVENTION

Bituminous paving mixes, containing aggregate and combustible asphalt binder, are widely used in the road construction industry. Federal and state guidelines require that paving mixes exhibit certain compositional properties to ensure the long-term durability of roadways constructed of such materials. As a result, it is necessary to test the paving mix composition to determine whether the requisite properties are present. For example, it is often necessary to determine the relative amounts of asphalt binder and aggregate, as well as the gradation of aggregate size.

Pyrolysis techniques, wherein the asphalt binder is combusted in order to separate the binder from the aggregate, are known in the art. Such techniques allow measurement of asphalt content, as well as aggregate gradation analysis. Conventional pyrolysis techniques utilize a furnace having electric heater plate elements. Heat energy is produced in the heater plates and transferred to a combustion chamber through conduction and convection. In this manner, the air in the combustion chamber is preheated to an elevated temperature, typically in excess of 500° C. Thereafter, a paving mix sample is inserted into the combustion chamber. Once inside the furnace, the paving mix sample is heated by conductive and convective heat transfer to a temperature of about 460–500° C. to achieve ignition of the asphalt binder. As the asphalt binder combusts, weight loss is measured using an internal weighing device incorporated into the furnace structure and final asphalt content is determined.

The conventional pyrolysis process has numerous drawbacks. First, the energy transfer from the heater plates to the paving mix sample is highly inefficient and requires the slow process of preheating the air in the furnace to an elevated temperature in order to ignite the paving mix sample. Depending on the type and manufacturer of the furnace, it can take up to several hours to preheat the furnace. Additionally, preheating the oven to ignition temperature and subsequent combustion of the sample can result in extended periods of elevated temperatures within the combustion chamber. These high temperatures can lead to thermal decomposition of the aggregate, resulting in loss of aggregate from the sample and reduction of the aggregate particle size, adversely effecting the accuracy of the analysis. To avoid loss of aggregate, a slow, smoldering type of combustion may be used to maintain a lower combustion chamber temperature. While this is somewhat effective in preventing thermal decomposition of aggregate, the lower combustion temperatures result in increased emission of excess carbon and other potential pollutants. Consequently, conventional furnaces generally require an afterburner to reduce pollutant discharge.

There is a need in the art for a method and apparatus for pyrolysis of a paving mix sample that efficiently transfers heat to the sample and produces relatively low levels of pollutants without the need for an afterburner.

SUMMARY OF THE INVENTION

The present invention provides a method and apparatus for pyrolysis of a paving mix sample that combusts the asphalt binder portion of the paving mix in a more efficient manner and with lower pollutant emissions than provided by conventional furnaces. In one embodiment, the present invention utilizes infrared radiation to ignite the asphalt binder and infrared radiation in combination with forced convection to efficiently combust the asphalt binder, while limiting aggregate loss and environmental pollution. Further, by adjusting the temperature of the infrared heater, as well as the air flow through the combustion chamber, the present invention provides a controlled combustion process that is faster and more energy efficient than conventional processes.

The apparatus of the present invention includes an oven having a bottom wall, a top wall, and side walls defining a combustion chamber. A sample support is provided within the combustion chamber for receiving and supporting a sample of paving mix. The apparatus may include a sample container positioned on the sample support and adapted for receiving a sample of paving mix. An infrared heater is mounted within the oven and arranged for emitting infrared radiation towards the sample holder so as to heat the sample of paving mix by means of radiation heat transfer. The apparatus includes both an air inlet and an outlet. The air inlet is positioned for admitting air into the combustion chamber and, preferably, at a location above the sample support. The outlet is positioned for discharging combustion gases from the combustion chamber, preferably at a location below the air inlet to thereby provide for the circulation of air and combustion gases generally downward through the combustion chamber.

In a preferred embodiment, the infrared heater is located in an upper portion of the combustion chamber and is oriented to direct infrared radiation generally downwardly at the sample holder. Further, the air inlet is preferably located in an upper portion of one of the side walls and the outlet is preferably located in the opposite side wall such that airflow in the chamber circulates in a generally downward and side-to-side manner.

A blower is located on the downstream side of the outlet and cooperates therewith for inducing flow into the combustion chamber via the inlet and out of the combustion chamber via the outlet. Preferably, the apparatus further comprises a variable speed blower controller operable for varying the blower speed during pyrolysis of the paving mix. Additionally, a plenum chamber is mounted on the outside of the combustion chamber and communicates therewith via the outlet. An exhaust flue connected to the plenum chamber allows discharge of exhaust gases from the plenum chamber. Preferably, the blower is mounted between the plenum chamber and the exhaust flue. The plenum chamber may include an adjustable air inlet vent for admitting ambient cooling air into the plenum chamber to mix with the exhaust gases entering the plenum chamber via the outlet.

The apparatus may further comprise a housing surrounding the oven and spaced from the top and side walls thereof, and also surrounding the plenum chamber. Preferably, the housing includes am air inlet vent for emitting ambient cooling air into the housing induced by the above-described blower.

A weighing device is operatively connected to the sample support for obtaining weight measurements of the sample during pyrolysis thereof In a preferred embodiment, a processor is operatively connected to the weighing device, and includes an instruction set for calculating weight loss during pyrolysis. In one embodiment, the apparatus comprises an external weighing device adapted for receiving a sample container and obtaining the empty weight and filled weight thereof Preferably, the external weighing device is operatively connected to the processor for communication of the empty weight and filled weight to the processor. The processor preferably includes a first data store for storing the empty weight and a second data store for storing the filled weight. The processor may further include a weight loss correction factor generator operable for calculating a weight loss correction factor.

The present invention also provides a method for assaying the asphalt content of a bituminous paving mix. The method includes placing a sample of a paving mix containing aggregate in a combustible asphalt binder in a sample container. The sample container is placed in a combustion chamber of an oven. The sample is then exposed to radiation from an infrared heater. The paving mix sample is heated by radiation heat transfer from the infrared heater to ignite and combust the asphalt binder. Airflow is introduced into the combustion chamber through an inlet to fuel the combustion of the asphalt binder and combustion gases resulting from the combustion are discharged through an outlet. The process of the present invention further includes adjusting at least one of the temperature of the infrared heater and the rate of airflow through the combustion chamber during the heating step.

In a preferred embodiment, the airflow through the combustion chamber is initially maintained at a relatively low rate to discharge combustion gases through the outlet until the approximate time of ignition of the asphalt binder. Thereafter, the rate of airflow is increased after ignition of the asphalt binder to draw heat into lower portions of the paving mix sample. Additionally, the temperature of the infrared heater can be rapidly decreased while maintaining the increased rate of airflow to cool the aggregate. Preferably, the airflow rate is adjusted by increasing or decreasing the rotational speed (rpm) of a blower operatively positioned to induce a flow of air through the combustion chamber.

In one embodiment, the method according to the present invention further comprises measuring the initial sample weight using a weighing device located external to the oven prior to placing the sample container in the combustion chamber. The initial sample weight is then measured using an internal weighing device operatively positioned within the oven. The sample weight determined by the external weighing device is communicated to a processor operatively connected to the internal weighing device. Thereafter, the two measured sample weights are compared to determine a weight loss correction factor. After combustion of the asphalt binder, the final weight of the paving mix may be measured using the internal weighing device. A corrected final weight may then be calculated by applying the weight loss correction factor to the measured final weight.

BRIEF DESCRIPTION OF THE DRAWINGS

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

The apparatus of the present invention is useful for combusting a sample of a combustible material and analyzing the resulting weight loss of the sample. For instance, the present invention can be used for pyrolysis of a bituminous paving mix containing aggregate and a combustible asphalt binder.

Figure 1:
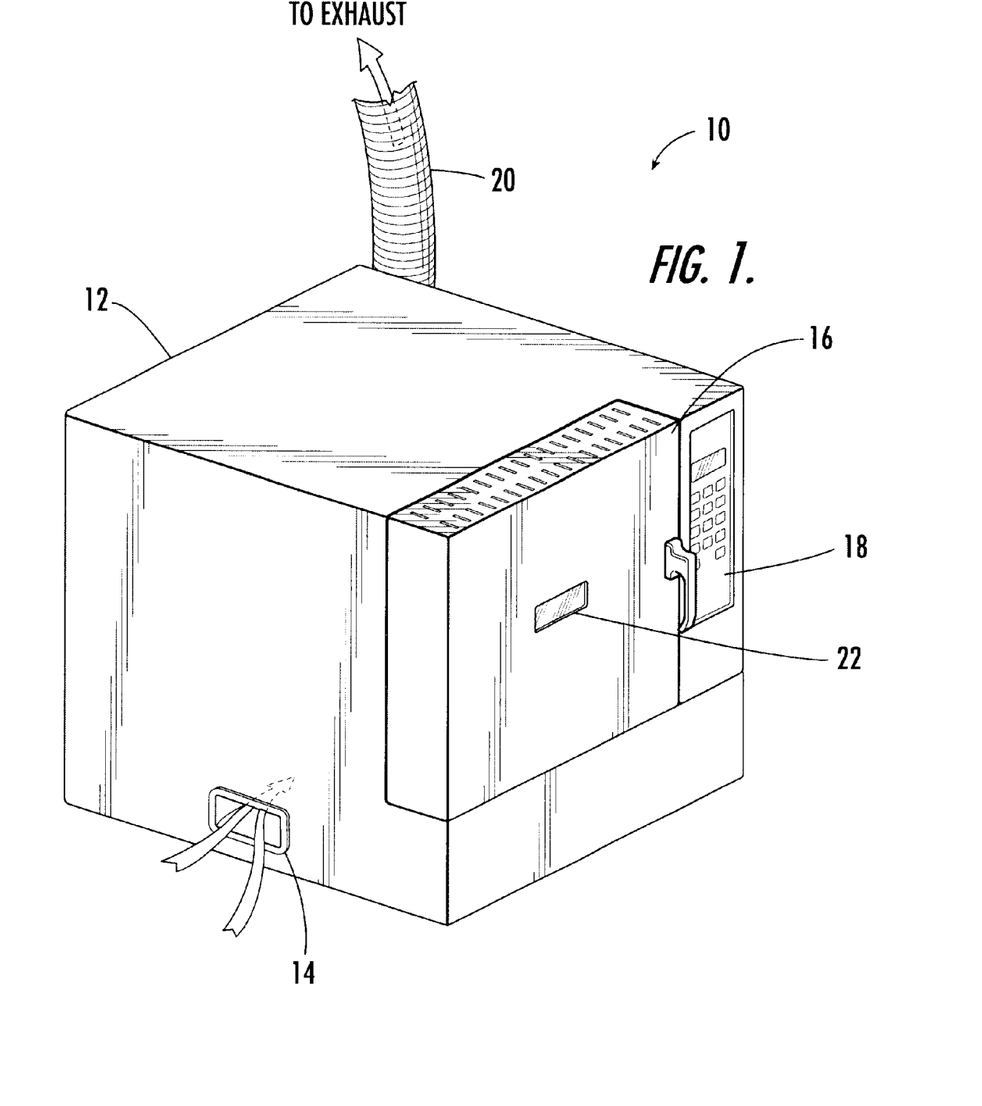
FIG. 1 is a perspective view of an embodiment of the apparatus of the present invention.
Figure 2:
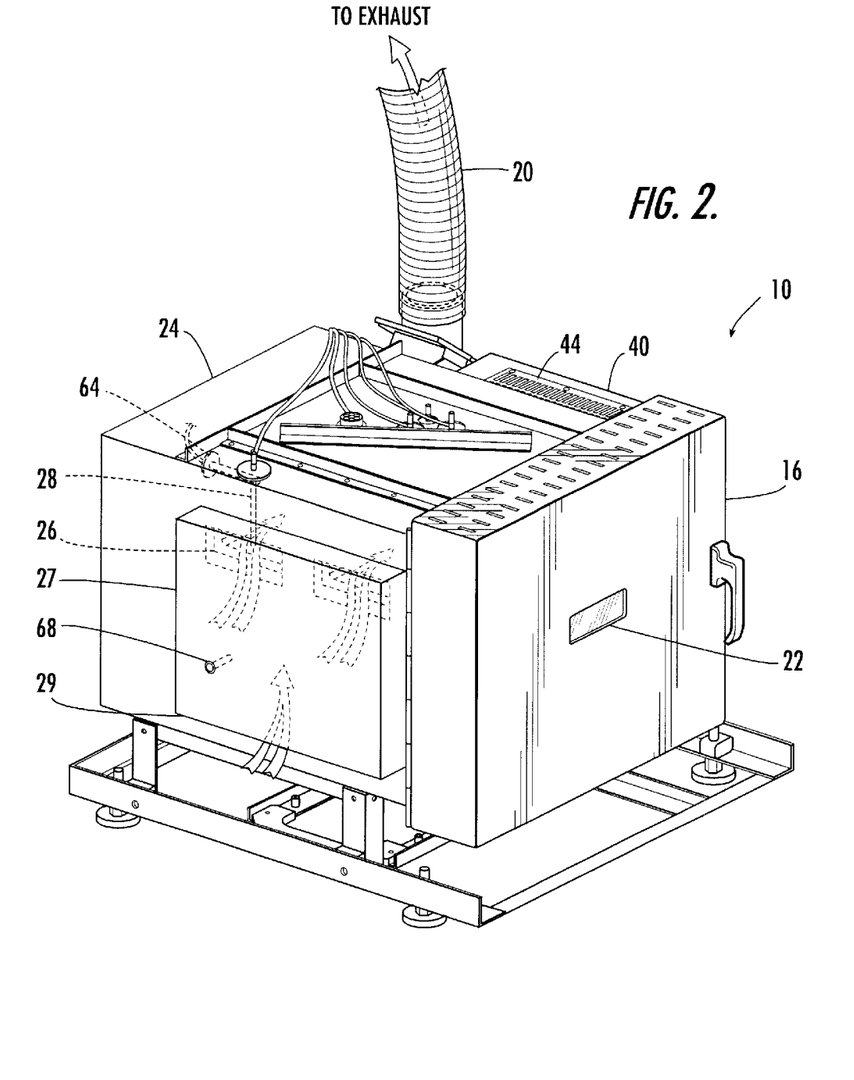
FIG. 2 is a perspective view of an embodiment of the apparatus of the present invention with the outer housing removed.

FIG. 1 illustrates an embodiment of an apparatus according to the present invention. As shown, the apparatus 10 includes an outer housing 12. Preferably, the housing 12 includes at least one air inlet vent 14 for admitting ambient cooling air into the housing. The apparatus 10 further includes a door 16 and a control panel 18. Preferably, the door 16 includes a window 22 that allows observation of the interior of an oven 24 (shown in FIG. 2). An embodiment of the present invention with the housing 12 removed is shown in FIG. 2. As shown, the housing 12 surrounds an oven 24 and a plenum chamber 40.

Figure 3:
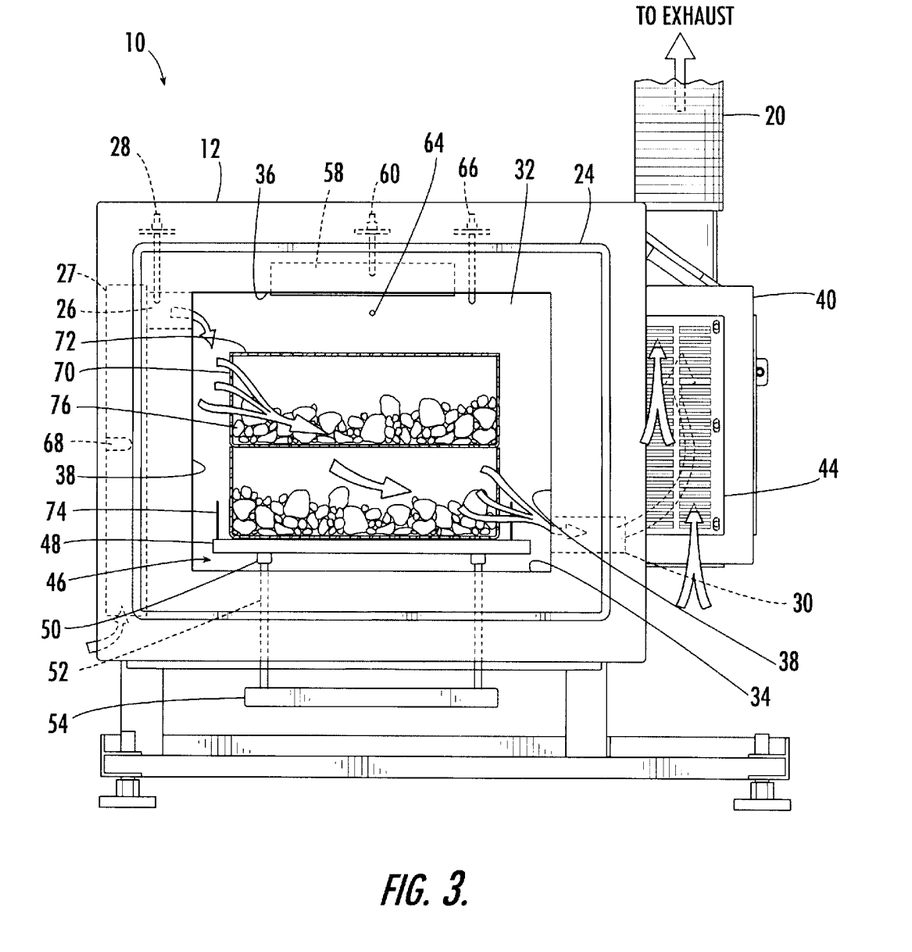
FIG. 3 is a front view of an embodiment of the apparatus of the present invention.

Now referring to FIG. 3, the oven 24 comprises a bottom wall 34, a top wall 36, and side walls 38, which collectively define a combustion chamber 32. Preferably, the interior of the combustion chamber 32 is at least partially lined with a layer of insulation. Preferably, the layer of insulation is a lightweight refractory material capable of withstanding the operating temperatures of the oven 24. For example, the insulation layer may comprise RATH ALTRA® KVS124 insulation manufactured by Rath Performance Fibers, Inc. of Wilmington, Del. The insulation increases process efficiency by reducing the loss of energy between process cycles.

A sample support 46 is provided within the combustion chamber 32 for receiving and supporting a sample of a combustible material, such as bituminous paving mix. In a preferred embodiment, the sample support comprises spaced apart rails 50 positioned above the bottom wall 34 and arranged for supporting a sample container 70. Preferably, a hearth plate 48 is overlying the rails 50 and operatively positioned for receiving and supporting a sample of paving mix. In one embodiment, the hearth plate 48 is constructed of an insulating material, such as RATH ALTRA® KVS124 manufactured by Rath Performance Fibers, Inc. of Wilmington, Del. Alternatively, the hearth plate 48 may comprise a conductive material, such as a metal.

The rails 50 are supported by posts 52. The lower ends of the post 52 are supported by weighing device 54 beneath the bottom wall 34 of the combustion chamber 32. Using the weighing device 54, a sample placed within the combustion chamber 32 may be continuously weighed during the pyrolysis procedure.

An infrared heater 58 is mounted within the oven 24 and arranged for emitting infrared radiation toward the sample support 46 so as to heat the sample by means of radiant heat transfer. Preferably, the heater 58 is located in an upper portion of the combustion chamber 32 and oriented to direct infrared radiation generally downwardly toward the sample support. Although the infrared heater 58 is shown mounted in the top wall 36 of the oven 24, the infrared heater could also be mounted in the side walls 38 and oriented to direct infrared radiation at the sample from the side without departing from the present invention. The infrared heater 58 may comprise any heater designed primarily to emit radiation in the infrared spectrum, as opposed to a heating element designed to transfer heat primarily through conduction and convection. The infrared heater 58 may use, for example, either gas heating or electric resistance heating to heat the heater to operating temperature. One suitable commercially available infrared radiation heater is the Watlow RAMAX® 2030 manufactured by Watlow Inc. of St. Louis, Mo. Preferably, the infrared heater 58 emits energy at a wavelength of from about 2 to about 15 $\mu$m. Typically, the operating temperature of the infrared heater 58 is about 600 to 1100° C. for emission of infrared energy of the desired wavelength spectra and intensity. The temperature of the infrared heater 58 is preferably monitored by a temperature sensor 60 embedded in the infrared heater.

The use of an infrared heater 58 provides several advantages over conventional furnaces. Unlike conventional pyrolysis furnaces, the present invention does not rely solely on heat conduction and convection to ignite the sample. Instead, radiation heating is used as the primary heating tool. In fact, the present invention can be used to ignite a sample solely using infrared radiation, without any preheating of the oven. Radiation heating heats the sample directly, rather than relying on transfer of heat from the air in the furnace to the sample. Thus, the present invention is more energy-efficient because use of the air in the furnace as an energy conduit is not required. Also, in a conventional furnace, hot air is constantly being replaced with cooler air, resulting in a large amount of heat loss through the exhaust. Such heat losses are greatly diminished by using the present invention. The lack of furnace preheating and use of direct heating of the sample results in shorter combustion times and a shorter overall process cycle as compared to conventional furnaces.

The lack of furnace preheating and shorter combustion times also result in lower combustion chamber temperatures than normally associated with conventional furnaces. Conventional furnaces must be preheated to the ignition temperature of the sample, typically about 450 to about 550° C. During combustion, temperatures in the combustion chamber of a conventional furnace can reach about 700° C. or higher. Moreover, these high temperatures can last for a significant portion of the process cycle, increasing the likelihood of damage to the aggregate. In contrast, the present invention maintains lower chamber temperatures by heating the sample directly. Typically, the sample temperature is maintained at a maximum temperature of about 500 to 600° C. and the average chamber temperature rarely exceeds 600° C. Further, the sample and chamber temperature maintain their maximum values for a short time, on the order of several minutes or less, thereby lessening the chance of aggregate degradation. Additionally, the infrared heater 58 is lighter than the heating blocks utilized by conventional furnaces.

Advantageously, a number of additional temperature measurements are made at various locations within the oven 24. For example, the apparatus 10 can include a temperature sensor 28 operatively positioned to measure the temperature of the air entering the air inlet 26. Further, one or more temperature sensors may be operatively positioned to measure the internal temperature of the combustion chamber 32. For example, as shown in FIGS. 2 and 3, a temperature sensor 66 may be placed so as to extend through the top wall 36 of the combustion chamber 32. In this position, temperature sensor 66 may be used to detect ignition of the sample. Additionally, a temperature sensor 64 may be mounted in the rear side wall 38 to measure combustion chamber temperature. The temperature sensors utilized in the apparatus 10 of the present invention may comprise any suitable temperature sensor known in the art, including thermocouples and thermistors.

In one embodiment, the temperature of the sample is also measured using a temperature sensor (not shown). Preferably, the sample temperature sensor comprises a non-contact infrared sensor mounted in the oven 24 and arranged for absorbing infrared radiation emitted from the sample for temperature measurement thereof As shown in FIG. 3, an air inlet 26 is positioned for emitting air into the combustion chamber 32 at a location above the sample support 46. Preferably, a baffle 27 is positioned to funnel air into the air inlet 26 by partially enclosing the air inlet. As shown, the baffle 27 has an opening 29 spaced apart from the air inlet 26 to funnel air into the enclosure created by the baffle and, subsequently, into the air inlet. Additionally, an outlet 30 is positioned for discharging combustion gases from the combustion chamber 32 at a location below the air inlet 26. In this manner, air and combustion gases within the combustion chamber 32 circulate generally downward through the combustion chamber. An airflow sensor 68 is operatively positioned to measure the rate of airflow through the combustion chamber. For instance, the airflow sensor 68 may be placed upstream of the air inlet 26. The air inlet 26 is preferably, although not necessarily, located in an upper portion of one of the sidewalls 38 and the outlet 30 is preferably located in a lower portion of the opposite side wall. In this manner, the flow of air through the combustion chamber 32 circulates both generally downward and side-to-side through the combustion chamber.

In a preferred embodiment, the general downward circulation of combustion gases within the chamber 32 caused by the relative placement of the air inlet 26 and outlet 30 increases the residence time of the combustion gases. This encourages absorption of infrared radiation by the combustion gases and reduces the level of pollutants leaving the combustion chamber. Natural convection currents carry the combustion gases upward from the burning sample and toward the infrared heater 58. However, the placement of the outlet 30 in the lower portion of the combustion chamber 32 requires the combustion gases to substantially reverse course to exit the chamber. Thus, the combustion gases remain in the chamber 32 for longer periods of time and, consequently, the gases are exposed to the infrared radiation given off by the heater 58 for longer periods of time. The infrared radiation is absorbed by the combustion gases, resulting in oxidation and decomposition of the pollutants therein. In this manner, pollutant levels in the combustion gases exiting the chamber 32 via the outlet 30 are reduced. For example, in some embodiments of the present invention, the pollution levels in the combustion gases are reduced by about 33% or more, as compared to conventional dual-chamber furnaces.

Figure 4:
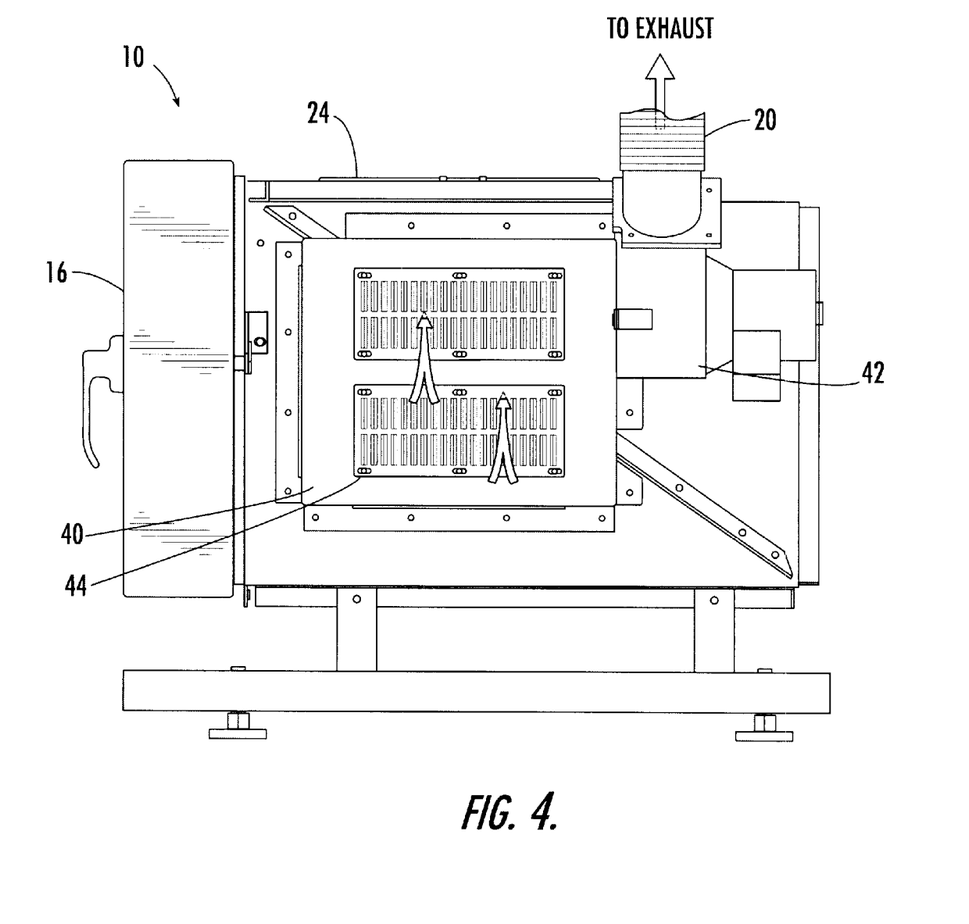
FIG. 4 is a side view of an embodiment of the apparatus of the present invention.

The apparatus 10 of the present invention further comprises a plenum chamber 40 mounted on the outside of the combustion chamber 32 and communicating therewith by the outlet 30. An exhaust flue 20 is connected to the plenum chamber for discharging exhaust gases therefrom. A blower 42, as shown in FIG. 4, is mounted between the plenum chamber 40 and the exhaust flue 20. The blower 42, which is located on the downstream side of the outlet 30, cooperates with the outlet for inducing flow into the combustion chamber 32 via the air inlet 26 and out of the combustion chamber via the outlet. The blower 42 may comprise any device capable of inducing airflow through the combustion chamber 32, such as a fan. In a preferred embodiment shown in FIG. 5, a variable speed blower controller 80 is operatively connected to the blower 42 for varying the blower speed during pyrolysis of the sample. Using the variable speed blower controller 80, the present invention allows introduction of a controlled convection component to the combustion process that further increases process efficiency, as described in greater detail below. Referring back to FIG. 4, the plenum chamber 40 preferably includes air inlet vents 44 for admitting ambient cooling air into the plenum chamber for mixing with the exhaust gases entering the plenum chamber via the outlet 30. In this manner, the exhaust gases leaving the combustion chamber 32 are cooled prior to contacting the blower 42. Preferably, the air inlet vents 44 are adjustable. For example, the air inlet vents 44 may comprise one or more adjustable vanes so that the flow of ambient cooling air entering the plenum chamber may be changed by adjusting the position of the vanes.

As described above, air flow through the combustion chamber 32 is induced by a blower 42, thereby providing a forced convection component of heat transfer that enhances pyrolysis of the sample. The forced convection is beneficial for several reasons. In a preferred embodiment, the generally downward flow of air through the combustion chamber 32 allows heat energy emitted by the burning material in a higher tier of the sample container 70 to be transferred to the sample material in a lower tier of the sample container, thereby igniting the material in the lower tier. The utilization of the energy emitted from one layer of material to ignite another layer enhances the energy efficiency of the apparatus 10. In addition, the downward movement of air through the combustion chamber 32 heats the air in the lower portion of the chamber and encourages complete combustion of the asphalt binder. In a preferred embodiment, the movement of airflow through the combustion chamber 32 also circulates in a side-to-side manner that minimizes the effect of flowing air on the weight measured by the weighing device 54. The forced movement of air through the chamber 32 also reduces soot formation on the walls of the chamber. Additionally, when a multi-tier sample basket is used, the forced movement of air through the chamber 32 reduces the temperature of a higher layer of the sample by carrying the flame generated by combustion of a lower layer of the sample away from the higher sample. The lower sample temperature discourages thermal decomposition of the aggregate, without resorting to the inefficient, smoldering type of combustion used in some conventional pyrolysis processes.

Referring to FIG. 3, a sample container 70 may be positioned on the sample support 46 and adapted for receiving a sample 76 of bituminous paving mix. Preferably, the sample container 70 comprises an openwork basket having at least two tiers oriented for arranging the sample 76 of paving mix in a plurality of thin layers. Alternatively, the sample container 70 may contain only a single tier. The openwork basket may be constructed of any suitable material, such as stainless steel. Preferably, the sample container 70 includes a perforated lid 72 which allows the sample 76 to be exposed to infrared radiation emitted from the infrared source 58 located above the sample container without substantial blocking of the radiation. The openwork basket embodiment of the sample container 70 allows air to reach the sample 76 for combustion of the asphalt binder. The openwork basket configuration also allows efficient heat transfer between the tiers such that heat given off by combustion of the sample 76 in one tier may be used to heat the sample located in an adjacent tier. Additionally, the sample container 70 may further include a catch pan 74 underlying the openwork basket to capture any material that falls through the perforated openings of the basket. One or more straps (not shown) can be used to retain the tiers of the openwork basket and affix the basket to the catch pan 74.

Figure 5:
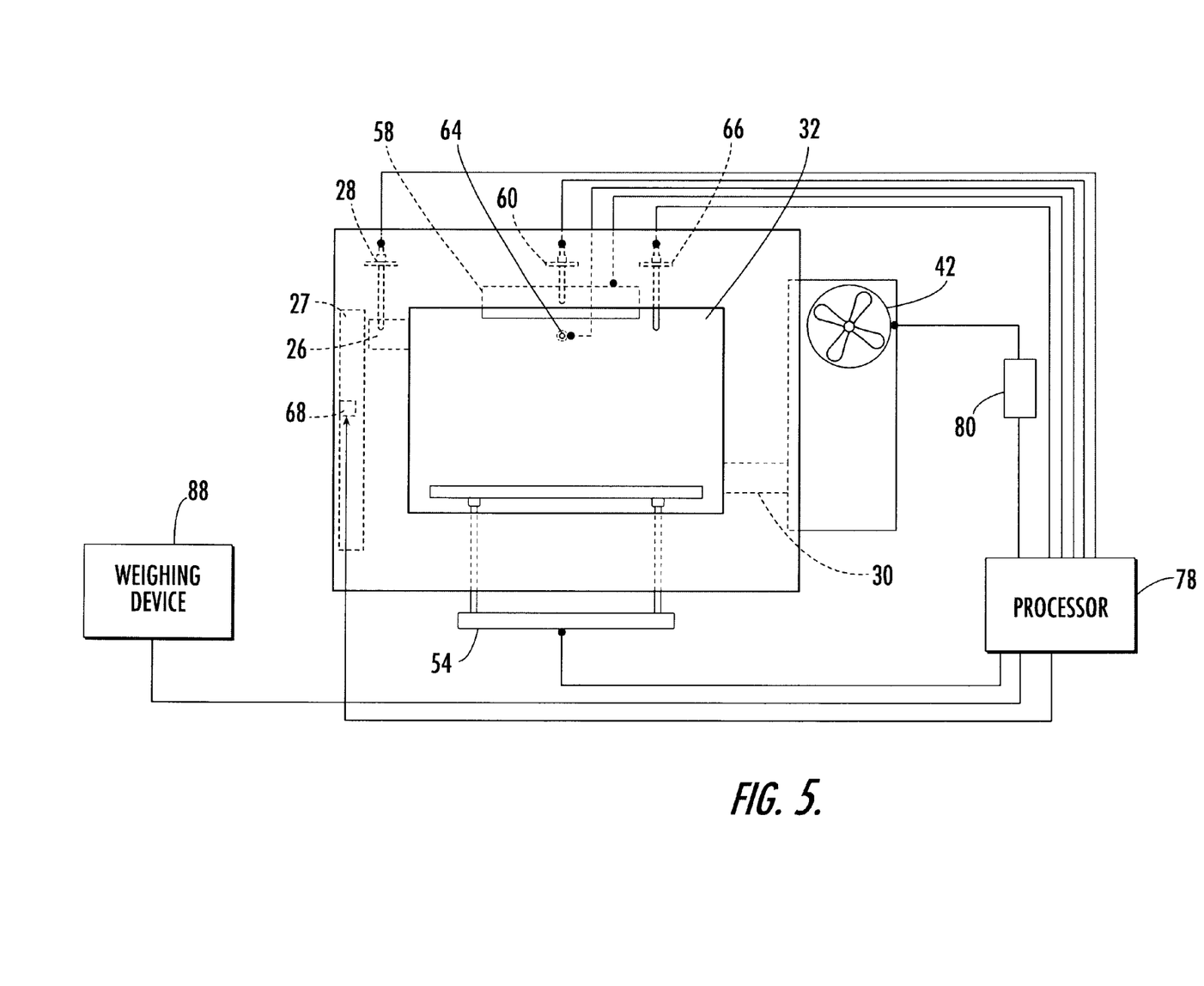
FIG. 5 is a schematic view of an embodiment of the apparatus of the present invention.

FIG. 5 illustrates a preferred process control configuration of the present invention. As shown, a processor 78 is operatively positioned for gathering data from various data sources within the apparatus. For example, the processor 78 is operatively connected to the weighing device 54 such that weight measurements may be communicated to the processor. Preferably, the processor 78 includes an instruction set for calculating weight loss during pyrolysis of a sample using data communicated from the weighing device 54. Additionally, the processor 78 is operatively connected to each of the temperature sensors, 28, 60, 64, and 66, and the airflow sensor 68, so that temperature and airflow measurements may be stored and analyzed for process control purposes, as described more fully below. Further, the processor 78 is operatively connected to the variable blower speed controller 80 such that the processor can manipulate the rotational speed of the blower 42 via the blower speed controller. Preferably, the processor 78 also keeps track of time during combustion of a sample, so that other process variables, such as weight and temperature, may be tracked as a function of time.

Additionally, in a preferred embodiment, the processor is operatively connected to an external weighing device 88 adapted for receiving a sample container and obtaining the empty weight and filled weight thereof In this manner, the empty weight and filled weight measured by the external weighing device 88 may be communicated to the processor 78. Preferably, the processor 78 includes a first data store and a second data store for storing the empty weight and filled weight, respectively.

Errors in calculation of the weight loss of the sample can occur due to non-equilibrium conditions created by placement of a relatively cold sample in a relatively hot furnace. In one embodiment, the processor 78 further includes a weight loss correction factor generator operable for calculating a weight loss correction factor using data in the data stores. For instance, the weight loss correction factor generator may comprise means for calculating the difference between the sample weight determined by the external weighing device 88 and the initial sample weight determined by the internal weighing device 54, the difference being the weight loss correction factor. The processor 78 may utilize hardware, software, or any combination thereof to analyze and manipulate the various data communicated to the processor.

In operation, the apparatus 10 of the present invention is useful for assaying the asphalt content of a bituminous paving mix. A sample of the paving mix may be placed in a sample container. The sample container may then be placed in the combustion chamber 32 of an oven 24. The sample is exposed to radiation from an infrared heater 58. The paving mix sample is heated by radiation heat transfer from the infrared heater 58 to ignite and combust the asphalt binder portion of the portion of the paving mix. As noted above, the present invention can ignite the asphalt binder portion of the sample using only infrared heating, without preheating of the combustion chamber 32. Airflow is introduced into the combustion chamber through an inlet 26 to fuel the combustion of the asphalt binder. Combustion gases produced in the combustion chamber are discharged through an outlet 30. During the combustion process, at least one of the temperature of the infrared heater 58 and the rate of airflow through the combustion chamber 32 is adjusted in order to minimize the time required to combust the asphalt binder and increase the efficiency of the combustion.

For example, the adjusting step may comprise maintaining the airflow through the combustion chamber at an initial relatively low rate to discharge combustion gases through the outlet until the approximate time of ignition of the asphalt binder. Until the ignition of the asphalt binder occurs, it is desirable to minimize airflow through the chamber that can lead to heat loss from the paving mix sample. Thus, for example, the airflow is maintained at a relatively low rate of about 0.0 to about 2.0 cfm. Once the sample is ignited, the rate of airflow can be increased through the combustion chamber 32 to draw heat into lower portions of the paving mix sample. The onset of combustion or ignition of the sample may be sensed using any method known in the art. For example, the approximate time of ignition can be detected by detecting a loss in weight or an increase in the rate of weight loss of the sample. As described above, the apparatus 10 is designed such that airflow through the combustion chamber 32 is drawn generally downward to the chamber such that heat given off by a layer of paving mix in an upper tier of the sample container 70 may be transferred to a layer of paving mix and a lower tier of the container. For example, the rate of airflow is increased incrementally, first to about 2.0 to about 5.0 cfm and thereafter to about 6.0 to about 10.0 cfm. Preferably, the rate of airflow through the chamber 32 is increased by increasing the rotation speed of the blower 42. By adjusting the airflow through the chamber 32, the present invention introduces a forced convection component to the combustion process that further increases process efficiency.

During combustion of the sample, the temperature of the infrared heater 58 may be decreased while maintaining an increased rate of airflow in order to cool the aggregate. For example, in one embodiment, the infrared heater 58 is initially operated at a temperature of about 600 to about 1100° C., preferably about 900 to about 1100° C., when the sample is placed in the combustion chamber and during initial combustion of the sample. Later during combustion, the heater temperature may be decreased incrementally. For example, the heater temperature may be decreased to about 750 to about 900° C. and thereafter to about 600 to about 750° C. In this manner, the temperature of infrared heater 58 is gradually reduced during the pyrolysis process to minimize loss of aggregate due to thermal decomposition.

When the sample is first placed in the chamber 32 and the initial weight is measured by the weighing device 54, it is desirable to maintain the airflow through the combustion chamber 32 at a relatively high rate. This is desirable to avoid development of a weight measurement offset due to differences in the rate of airflow through the chamber during the initial measurement of the empty weight of the sample and during later measurements of the weight as the sample burns. Thus, in one embodiment, the airflow to the combustion chamber 32 is maintained at a rate of about 1.0 to about 6.0 cfm for at least about 30 seconds after placing the sample container 70 in the combustion chamber. The initial weight of the sample is determined while the airflow is maintained at the above rate. The final weight of the paving mix is determined after combustion of the asphalt binder or other combustible portion of the sample. In addition to the weight of the sample, the temperature of the sample can also be measured while the sample is combusted.

The initial sample weight may also be measured prior to placement of the sample container in the combustion chamber 32 using an external weighing device 88. Once the sample container is placed in a combustion chamber 32, the initial sample weight is measured using the internal weighing device 54. In a preferred embodiment, the sample weight determined by the external weighing device 88 is communicated to the processor 78, which is also operatively connected to the internal weighing device 54. Thus, the processor 78 may compare the two measured sample weights to determine a weight loss correction factor.

To determine the initial sample weight using the external weighing device 88, the weight of an empty sample container 70 is first measured using the external weighing device. A sample of a bituminous paving mix is in place in the sample container 70.

Thereafter, the filled weight of the sample container 70 is measured using the external weighing device 88. Using the measured weight of the sample container and the filled weight of the sample container, a first initial weight of the sample may be determined. The sample container is placed in the combustion chamber 32 of an oven 24. The filled weight of the sample container 70 may then be measured again using an internal weighing device 54 operatively positioned within the oven 24. The difference between the initial weight calculated using the external weighing device 88 and the initial weight calculated using the internal weighing device 54 is a weight loss correction factor. Thereafter, the sample may be combusted using the infrared heater 58 as described above. After the combustible portion of the sample is removed, the final weight of the paving mix sample may be measured using the internal weighing device 54. The weight loss correction factor may be applied to the measured final weight to obtain a corrected final weight.

EXAMPLE

This is an example of one process configuration. However, as will be appreciated, the airflow rates and infrared heater temperatures may differ from the values given below without departing from the present invention. A 1200-gram asphalt sample was placed in an embodiment of the apparatus of the present invention. The infrared heater was operating at 1000° C. The following process was used to combust the sample:

1. The fan was set at a maximum speed of 4.45 cfm.
2. The internal weighing device determined an initial sample weight.
3. Fan speed was reduced to a very low value (1–2 cfm) until ignition. The low value was chosen such that the airflow through the chamber was just high enough to ensure that the combustion gases escape through the outlet rather than through the air inlet.
4. After one minute, fan speed was increased to a medium value of about 3.4 cfm to fuel the fire.
5. After one minute, the fan speed was increased again to an approximately maximum speed of 4.45 cfm to fuel the fire and cool the aggregate.
6. After seven minutes, the infrared heater temperature was reduced from 1000° C. to 900° C.

7. At 14 minutes into the process, the infrared heater temperature was reduced from 900° C. to 800° C. The fan was still at maximum process speed.

8. At the 20-minute mark, the asphalt had a weight loss slope of 0.1 g/min. (the cutoff criteria) and the process was ended.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for pyrolysis of a bituminous paving mix containing aggregate and a combustible asphalt binder, said apparatus comprising:

an oven having a bottom wall, a top wall, and side walls defining a combustion chamber;

a sample support provided within said combustion chamber for receiving and supporting a sample of the paving mix;

an infrared heater mounted within said oven and arranged for emitting infrared radiation toward said sample support so as to heat the sample of paving mix to combustion by means of infrared radiation heat transfer;

an air inlet positioned for admitting air into the combustion chamber;

an outlet positioned for discharging combustion gases from the combustion chamber to thereby provide for the circulation of air and combustion gases through the combustion chamber; and a blower cooperating with said combustion chamber for causing air flow into the combustion chamber via said inlet and out of said combustion chamber via said outlet.

2. The apparatus according to claim 1, further comprising a variable speed blower controller cooperating with said blower for varying the blower speed during the pyrolysis of the paving mix.

3. The apparatus according to claim 2, including means cooperating with said blower controller for operating the blower at a lower flow rate during an initial stage of the pyrolysis and at an increased flow rate during a subsequent stage of the pyrolysis.

4. The apparatus according to claim 1, wherein said blower is located on the downstream side of said outlet and cooperates therewith for inducing flow into the combustion chamber via said inlet and out of said combustion chamber via said outlet.

5. The apparatus according to claim 4, further comprising a plenum chamber mounted on the outside of said combustion chamber and communicating therewith via said outlet, and an exhaust flue connected to said plenum chamber for discharging exhaust gases therefrom, and wherein said blower is mounted between said plenum chamber and said exhaust flue.

6. The apparatus according to claim 5, further comprising an air inlet vent in said plenum chamber for admitting ambient cooling air into the plenum chamber for mixing with the exhaust gases entering the plenum chamber via said outlet.

7. The apparatus according to claim 6, wherein said air inlet vent comprises at least one adjustable vane for adjusting the amount of air entering said vent.

8. The apparatus according to claim 5, further comprising a housing surrounding said oven and spaced from said top and side walls thereof, said housing also surrounding said plenum chamber, and including an air inlet vent in said housing for admitting ambient cooling air into the housing induced by said blower.

9. The apparatus according to claim 1, wherein said heater is located in an upper portion of said combustion chamber and is oriented to direct infrared radiation generally downwardly at said sample support.

10. The apparatus according to claim 1, wherein said air inlet is located in an upper portion of one of said side walls, and said outlet is located below said air inlet on the opposite side wall.

11. The apparatus according to claim 1, further comprising an airflow sensor operatively positioned to measure rate of airflow through said combustion chamber.

12. The apparatus according to claim 11, wherein said airflow sensor is positioned upstream of said air inlet.

13. The apparatus according to claim 1, further comprising a sample container positioned on said sample support and adapted for receiving a sample of the bituminous paving mix and a weighing device operatively connected to said sample support for obtaining weight measurements of the sample during pyrolysis thereof.

14. The apparatus according to claim 13, further comprising a processor operatively connected to said weighing device, and including an instruction set in said processor for calculating weight loss during pyrolysis.

15. The apparatus according to claim 14, further comprising:

an external weighing device adapted for receiving said sample container and obtaining the empty weight and filled weight thereof, said external weighing device being operatively connected to said processor for communication of the empty weight and filled weight to said processor, and wherein said processor includes a first data store for storing the empty weight and a second data store for storing the filled weight.

16. The apparatus according to claim 14, wherein said processor includes a weight loss correction factor generator operable for calculating a weight loss correction factor using the data in said first data store and said second data store.

17. The apparatus according to claim 16, wherein said weight loss correction factor generator comprises means for calculating the difference between the sample weight determined by said external weighing device and the sample weight determined by said internal weighing device, the difference being the weight loss correction factor.

18. The apparatus according to claim 13, wherein said sample container comprises an openwork basket having at least two tiers oriented for arranging the sample of bituminous paving mix in a plurality of thin layers for pyrolysis.

19. The apparatus according to claim 18, wherein said basket includes a perforated lid for exposing the sample to infrared radiation emitted by said infrared heater.

20. The apparatus according to claim 1, further comprising a temperature sensor operatively positioned within said oven for measuring the temperature of a sample of paving mix.

21. The apparatus according to claim 20, wherein said temperature sensor comprises a non-contact infrared sensor.

22. The apparatus according to claim 1, wherein said sample support comprises spaced apart rails positioned above said bottom wall and a hearth plate overlying said rails and operatively positioned for receiving and supporting a sample of paving mix.

23. The apparatus according to claim 1, wherein said heater emits energy at a wavelength of from about 2 to about 15 µm.

24. An apparatus for pyrolysis of a bituminous paving mix containing aggregate and a combustible asphalt binder, said apparatus comprising:

an oven having a bottom wall, a top wall, side walls and an access door defining a combustion chamber;

a sample support provided within said combustion chamber;

a sample container for receiving and supporting a sample of the paving mix, said sample container being positionable on said sample support;

a weighing device operatively connected to said sample support for obtaining weight measurements of the sample during pyrolysis thereof;

an infrared heater mounted within said oven oriented to direct infrared radiation at said sample support so as to heat the sample of paving mix to combustion by means of infrared radiation heat transfer;

an air inlet positioned for admitting air into the combustion chamber;

an outlet for discharging combustion gases from the combustion chamber, said outlet being positioned in spaced relation from said air inlet to thereby provide for the circulation of air and combustion gases generally through the combustion chamber;

a plenum chamber mounted on the outside of said combustion chamber and communicating therewith via said outlet, an exhaust flue connected to said plenum chamber for discharging exhaust gases therefrom; and a blower mounted between said plenum chamber and said exhaust flue and operable for inducing a flow of air into the combustion chamber via said air inlet and for drawing exhaust gases from the combustion chamber into said plenum chamber via said outlet.

25. The apparatus according to claim 24, further comprising a variable speed blower controller operable for varying the blower speed during the pyrolysis of the paving mix.

26. The apparatus according to claim 25, further comprising means cooperating with said blower controller for operating the blower at a lower flow rate during an initial stage of the pyrolysis and at an increased flow rate during a subsequent stage of the pyrolysis.

27. The apparatus according to claim 24, wherein said heater is located in an upper portion of said combustion chamber and is oriented to direct infrared radiation generally downwardly at said sample support.

28. The apparatus according to claim 24, wherein said outlet is positioned at a location below said air inlet to thereby provide for the circulation of air and combustion gases generally downwardly through the combustion chamber.

29. The apparatus according to claim 24, wherein said air inlet is located in an upper portion of one of said side walls, and said outlet is located on the opposite side wall.

30. An apparatus for pyrolysis of a bituminous paving mix containing aggregate and a combustible asphalt binder, said apparatus comprising:

an oven having a bottom wall, a top wall, side walls and an access door defining combustion chamber;

a sample support provided within said combustion chamber;

a multi-tier sample basket for receiving a sample of the bituminous paving mix and arranging the sample in a plurality of thin layers for pyrolysis, said sample basket being removably positionable within the oven on said sample support;

an internal weighing device operatively connected to said sample support for obtaining weight measurements of the sample during pyrolysis thereof;

an infrared heater mounted within said oven in an upper portion of said combustion chamber and oriented to direct infrared radiation generally downwardly at said sample support so as to heat the sample of paving mix to combustion by means of infrared radiation heat transfer;

an air inlet positioned for admitting air into the combustion chamber at a location above said sample support;

an outlet positioned for discharging combustion gases from the combustion chamber at a location below said air inlet to thereby provide for the circulation of air and combustion gases generally downwardly through the combustion chamber; and a blower located on the downstream side of said outlet and cooperating therewith for inducing a flow of air into the combustion chamber via said air inlet and for drawing exhaust gases from the combustion chamber via said outlet.

31. The apparatus according to claim 30, further comprising a housing surrounding said oven and spaced from said top, side and bottom walls thereof, and including an air inlet vent in said housing for admitting ambient cooling air into the housing induced by said blower.

32. The apparatus according to claim 31, wherein said weighing device is located between the bottom wall of said oven and a lower wall of said housing, and wherein said air inlet vent is so positioned and arranged as to direct ambient cooling air induced by said blower into contact with said weighing device for cooling the same.

33. The apparatus according to claim 30, further comprising a processor operatively connected to said weighing device, and including an instruction set in said processor for calculating weight loss during pyrolysis.

34. The apparatus according to claim 33, further comprising:

an external weighing device adapted for receiving said sample container and obtaining the empty weight and filled weight thereof, said external weighing device being operatively connected to said processor for communication of the empty weight and filled weight to said processor, wherein said process comprises a first data store for storing the empty weight and a second data store for storing the filled weight.

35. The apparatus according to claim 34, wherein said processor includes a weight loss correction factor generator operable for calculating a weight loss correction factor using the data in said first data store and said second data store.

36. The apparatus according to claim 35, wherein said weight loss correction factor generator comprises:

means for calculating the difference between the sample weight determined by said external weighing device and the sample weight determined by said internal weighing device, the difference being the weight loss correction factor.

37. A method for assaying the asphalt content of a bituminous paving mix, said method comprising:

placing a sample of a bituminous paving mix containing aggregate and a combustible asphalt binder in a sample container;

placing the sample container with the sample of bituminous paving mix in a combustion chamber of an oven;

exposing the sample to radiation from an infrared heater;

heating the paving mix sample by infrared radiation heat transfer from the infrared heater to ignite and combust the asphalt binder;

introducing airflow into the combustion chamber through an inlet to fuel the combustion of the asphalt binder;

discharging combustion gases from the combustion chamber through an outlet;

adjusting at least one of the temperature of the infrared heater and the rate of airflow through the combustion chamber during said heating step.

38. The method according to claim 37, wherein said adjusting step comprises:

maintaining the airflow through the combustion chamber at an initial relatively low rate for an initial period and increasing the rate of airflow through the combustion chamber during a subsequent period.

39. The method according to claim 38, wherein said adjusting step comprises:

maintaining airflow through the combustion chamber at a preliminary relatively high rate for at least about 30 seconds after placing the sample container in the combustion chamber and determining the initial weight of the sample with the airflow at said preliminary relatively high rate, and thereafter reducing the airflow to said initial relatively low rate.

40. The method according to claim 38, further comprising decreasing the temperature of the infrared heater while maintaining an increased rate of airflow to cool the aggregate after said step of increasing the rate of airflow.

41. The method according to claim 40, wherein said step of decreasing the temperature of the infrared heater comprises decreasing the temperature of the infrared heater after the sample is undergoing combustion.

42. The method according to claim 38, wherein said step of increasing the rate of airflow comprises increasing the rotation speed of a blower operatively positioned to induce a flow of air through the combustion chamber.

43. The method according to claim 37, further comprising the step of preheating the infrared heater to about 600 to about 1100° C. prior to said step of placing the sample container in the combustion chamber.

44. The method according to claim 37, further comprising the step of 10 determining the final weight of the paving mix sample after combustion of the asphalt binder.

45. The method according to claim 37, further comprising the step of measuring the temperature of the paving mix sample during said heating step.

46. The method according to claim 37, further comprising the steps of:

measuring the initial sample weight using a weighing device located external to the oven prior to placing the sample container in the combustion chamber;

measuring the initial sample weight using an internal weighing device operatively positioned within the oven;

communicating the sample weight determined by the external weighing device into a processor operatively connected to the internal weighing device; and comparing the two measured sample weights to determine a weight loss correction factor.

47. A method for assaying the asphalt content of a bituminous paving mix, said method comprising:

placing a sample of a bituminous paving mix containing aggregate and a combustible asphalt binder in a sample container;

placing the sample container with the sample of bituminous paving mix a combustion chamber of an oven;

exposing the sample to radiation from an infrared heater;

heating the paving mix sample by radiating heat transfer from the infrared heater to ignite and combust the asphalt binder;

introducing airflow into the combustion chamber through an inlet to fuel the combustion of the asphalt binder;

discharging combustion gases from the combustion chamber through an outlet;

maintaining the airflow through the combustion chamber at an initial relatively low rate;

sensing the onset of combusting of the asphalt binder; and in response thereto increasing the rate of airflow through the combustion chamber during a subsequent period.

48. The method according to claim 47, wherein said step of sensing the onset of combustion comprises detecting a loss in the weight of the sample.

49. A method for assaying the asphalt content of a bituminous paving mix by combustion in an oven, said method comprising:

measuring the weight of an empty sample container using an external weighing device;

placing a sample of a bituminous paving mix containing aggregate and a combustible asphalt binder in the sample container;

measuring the filled weight of the sample container using a weighing device located external to the oven;

determining a first initial weight of the sample using the weight of the empty sample container and the externally-measured filled weight of the sample container;

placing the sample container with the sample of bituminous paving mix in a combustion chamber of the oven;

measuring the filled weight of the sample container using an internal weighing device operatively positioned within the oven;

determining a second initial weight of the sample using the weight of the empty sample container and the internally-measured filled weight of the sample container;

determining the difference between the first initial weight and the second initial weight, the difference being a weight loss correction factor;

exposing the sample to radiation from an infrared heater;

heating the paving mix sample by radiation heat transfer from the infrared heater to ignite and combust the asphalt binder;

introducing airflow into the combustion chamber through an inlet to fuel the combustion of the asphalt binder;

discharging combustion gases from the combustion chamber through an outlet;

measuring the final weight of the paving mix after combustion of the asphalt binder using the internal weighing device; and applying the weight loss correction factor to the measured final weight to obtain a corrected final weight.

* * * * *

UNITED STATES PATENT AND TRADEMARK OFFICE
CERTIFICATE OF CORRECTION

PATENT NO. : 6,440,746 B1
DATED : August 27, 2002
INVENTOR(S) : Troxler et al.

It is certified that error appears in the above-identified patent and that said Letters Patent is hereby corrected as shown below:

Column 16,
Line 5, after "mix" insert -- in --;
Line 7, "radiating" should read -- radiation --;
Line 16, after "sensing the onset of," "combusting" should read -- combustion --.

Signed and Sealed this

Twenty-eighth Day of January, 2003

JAMES E. ROGAN
*Director of the United States Patent and Trademark Office*